United States Patent [19]
Adamowicz et al.

[11] 4,335,214
[45] Jun. 15, 1982

[54] PROCESS FOR PURIFYING PARTICLES OF BIOLOGICAL ORIGIN, PARTICULARLY THE SURFACE ANTIGEN OF THE VIRUS OF HEPATITIS B (AGHBS)

[75] Inventors: Philippe J. Adamowicz, Garches; Alberte Platel née Bonnet, La Garenne Colombes; Ludwig Muller, Plessis Robinson, all of France

[73] Assignee: Institut Pasteur, Paris, France

[21] Appl. No.: 213,315

[22] Filed: Dec. 5, 1980

[30] Foreign Application Priority Data

Dec. 7, 1979 [FR] France ................. 79 30135

[51] Int. Cl.³ .................. A61K 39/12; C12K 7/00
[52] U.S. Cl. ................. 435/239; 260/112 B; 424/89; 210/787; 210/805
[58] Field of Search ......... 424/89; 210/787–789, 210/927, 805, 905, 781; 260/112 B; 435/239, 7

[56] References Cited

U.S. PATENT DOCUMENTS

| | | | |
|---|---|---|---|
| 3,838,144 | 9/1974 | Leach | 424/89 |
| 3,951,937 | 4/1976 | Vnek et al. | 424/89 |
| 4,024,243 | 5/1977 | McAleer et al. | 260/112 B |
| 4,088,748 | 5/1978 | McAleer et al. | 424/89 |
| 4,102,996 | 7/1978 | McAleer et al. | 435/7 |
| 4,217,418 | 8/1980 | McAleer et al. | 424/89 |

Primary Examiner—Benoît Castel
Attorney, Agent, or Firm—Weiser, Stapler & Spivak

[57] ABSTRACT

The invention relates to a process for purifying biological particles, particularly for purifying the surface antigen (HBs) of the hepatitis B virus. A suspension of this HBs antigen is subjected to rate zonal banding in a gradient inside a centrifuge equipped with a continuous-flow core. At the same time as the centrifugation operation is carried out, the suspension of particles to be purified is caused to circulate in a closed circuit in which the centrifuge is inserted. The band containing the purified biological particles is then collected in a way known per se.

16 Claims, 2 Drawing Figures

PROCESS FOR PURIFYING PARTICLES OF BIOLOGICAL ORIGIN, PARTICULARLY THE SURFACE ANTIGEN OF THE VIRUS OF HEPATITIS B (AGHBS)

The invention relates to a process for purifying particles of biological origin, particularly particles having antigenic properties, for example of viral or subviral origin. The invention applies with particular advantage to the purification of the surface antigen of the virus of hepatitis B. Generally, it is of quite special interest for purifying such biological particles which are characterized by a very low molecular weight (or particulate weight in the case of ordered or organized assemblies of molecules), even if it is but about twice that of impurities having the highest molecular weights, which are likely to accompany them. Such may be the case particularly with the HBs (or AgHBs) antigen, whose particulate weight is of the order of 2,000,000, which may be obtained from blood serums or plasmas, having, if necessary, been subjected to preliminary purification treatments, aiming for example at separating the major part of the immunocomplexes and at least a part of the lipoproteins which accompanied it in the initial plasma or serum.

Generally, the invention further applies also to the purification of biological particles characterized by a given mass/volume ratio or contained within a given range of mass/volume ratios, by separation of contaminants having a distinct, particularly higher, mass/volume ratio or density, even if these contaminants are characterized by lower molecular weights (for particulate weights).

The improved process of the invention aims at taking advantage of known techniques using zonal rate fractionation (or zonal rate banding), this process consisting in subjecting a solution or suspension, preferably concentrated and preferably also partially purified, to ultracentrifugation in contact with a liquid medium comprising a density gradient whose end values are preferably on both sides of those which correspond to the mass/volume ratios of the biological particles to be separated, for example the range of mass/volume ratios 1.17 to 1.20 per $cm^3$ in the case of the HBs antigen in a cesium chloride solution. If the rate zonal banding is operated at a speed and for a time adjusted so as to produce a differentiated migration under the effect of the centrifugal force of the biological particles on the one hand, and of the contaminants, on the other hand, one may thereafter proceed in a known manner with the separation of the centrifugation bands containing the viral particles then impoverished in contaminants, on the one hand, and of those containing essentially the separated contaminants, on the other hand.

In a certain way the invention may also be considered as an improvement to the process including isopycnic banding of said biological particles, such process consisting in placing a solution or a dispersion preferably concentrated and also preferably partially purified with a density gradient whose extreme densities are on both sides of the density values corresponding to the mass/volume ratio (or to the range of mass/volume ratios) of the viral particles to be purified. It is known that, in this technique, the biological particles under consideration then tend, when the centrifugation is sufficiently thorough, to be immobilized in a band of the gradient whose density or density range (isodense band) corresponds to the mass/volume ratio or the mass/volume ratio range of said particles, the latter remaining "trapped" in this band, even if the centrifugation is continued further.

The isopycnic banding technique which has proven to be particularly advantageous for concentrating and purifying biological particles of high molecular or particulate weight, for example viral particles such as the influenza virus whose molecular weights is of the order of 100,000,000, may be of small economic interest when the biological particles to be separated, such as the HBs antigen, have a relatively small particulate weight, since the migration speed of the latter particles within this gradient is then particularly low. The concentration of these particles in the isodense band then implies prolonged centrifugation times. To this economical disadvantage may be added that resulting from the equilibrium possibly attained between migration distances of the biological particles to be purified, on the one hand, and of a part at least of the contaminants, on the other hand, especially when the latter are characterized by mass/volume ratios greater than those of the biological particles. In fact, though these contaminants of lower molecular weight were able in a first stage to migrate "less quickly" than the purified biological particles, because of their lower molecular mass (a phenomenon of which advantage is taken in zone rate banding) these contaminants are then able to catch up with, even overtake, the isodense band in which the biological particles to be purified are concentrated, if the centrifugation is continued. This may particularly take place when the HBs antigen concentrates were insufficiently prepurified beforehand, since an isopycnic banding of an HBs antigen concentrate in a centrifugal machine of the type commercialized under the name "ELECTRONUCLEONICS" of the type known under the designation "K" or "RK", within a density gradient, at a centrifugation speed of 35,000 revolutions per minute (rpm) may require from 16 to 20 hours. This will then result in low productivity per unit of time (considering the particularly high cost of the equipment required) and considerable residual contamination, particularly by plasma macroglobulins. This may further render impossible, when the biological particles to be purified have a low particulate weight, continuous isopycnic banding operations, that is under continuous feeding of the rotor with the suspension or solution to be treated and the continuous discharge of the effluents (open circuit), with the above mentioned type of equipment under the usual conditions applied to molecules or aggregates of molecules having high particulate weights.

Consequently the invention aims at overcoming at least partially the preceding difficulties, particularly to provide a process for the purification of biological particles, even of relatively small molecular weights more particularly of the HBs antigen, by taking advantage of the technical possibilities offered by the processes of the type which have been recalled above, so as to obtain products of high purity under favorable economic conditions, particularly because of the considerable reduction in centrifugation times required.

The process of the invention which comprises the operation consisting in subjecting a solution or suspension of biological particles, such as the biological particles to be concentrated or purified, for example HBs antigen concentrates, to at least one rate zonal banding under centrifugation in a gradient inside a centrifuge whose rotor is equipped with a continuous-flow core, is characterized in that, at the same time as the centrifugation operation is carried out, the solution or suspension of particles to be purified is caused to flow in a closed circuit in which the centrifuge is inserted, particularly by means of a pump or similar (for example a perilstatic pump), established in a closed circuit outside the centrifuge.

The process of the invention thus enables any same part of the suspension or solution treated to flow or pass several times through the centrifuge, whereby part of the particles contained in said part of suspension or solution is then collected or caught by the density gradient at each passage.

The centrifuge is advantageously of the type commercialized by the ELECTRO-NUCLEONICS, INC. COMPANY for example of the type designated by the letters "K" or "RK".

Figure 1:
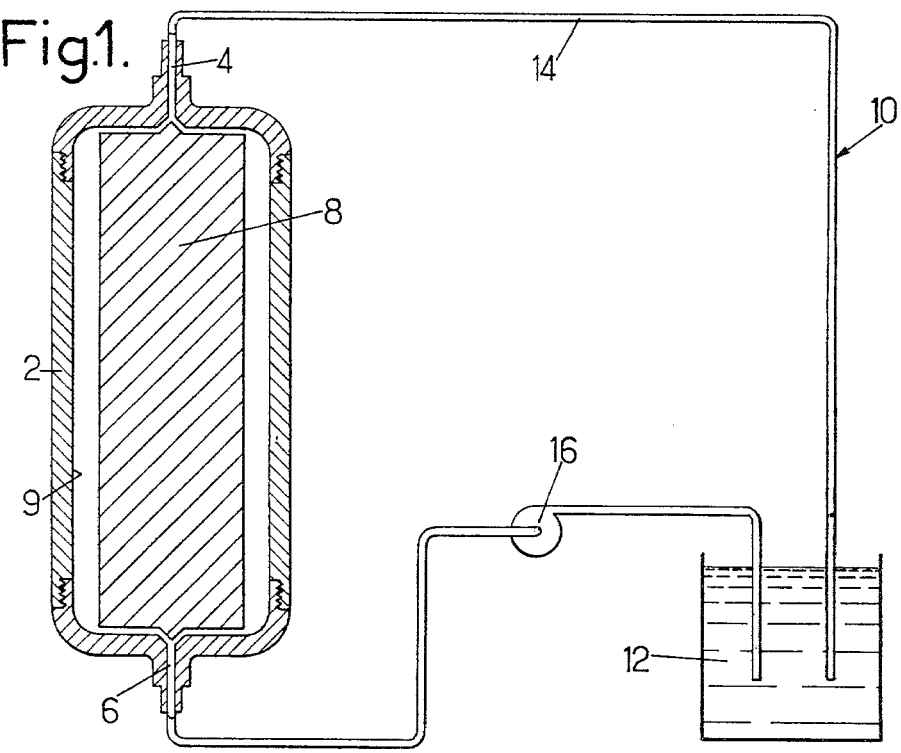
FIG. 1 is a simplified diagram showing by way of example the conditions under which such a closed flow circuit may be formed.

In FIG. 1 there is shown schematically the rotor of the "ELECTRO-NUCLEONICS K" or "RK" type centrifuge. The latter comprises in a manner known per se a rotor 2 forming the enclosure into which the gradients and the dispersions or solutions to be treated by centrifugation are to be fed, either from the top at 4, or from the bottom at 6. This rotor is equipped in a way known per se with a continuous-flow core 8. The inlet 4 and outlet 6 (which may be inverted for the flow direction of the suspension or of the solution of particles to be purified has no effect on the operating principle of the whole) are connected in a circuit shown schematically at 10, in which is inserted a container 12 containing a volume of solution or suspension to be treated in accordance with the invention, in addition to the quantities of solution or suspension which flow in the inner space defined between the internal walls of the rotor and the core 8 and the piping 14 of the closed circuit 10. A pump 16 of known type and suitable for circulating such solutions or suspensions is inserted in circuit 10.

The circulation of the solution or suspension effected at the same time as the centrifugation has the important advantage that it is possible to treat in a single centrifugation operation a greater quantity of suspension or solution that that which could be treated when working with a fixed charge (discontinuously), especially if it is taken into consideration that a considerable proportion of the inner capacity of the rotor is occupied by the gradient which will have been introduced therein beforehand (for example preferably of at least 9/10 of said inner capacity in the case of the purification of the HBs antigen).

It will be appreciated that a part of the amount of particles to be purified and of some impurities contained in the circulating liquid will tend, under the effect of the centrifugation, to remain in the enclosure and to move to and into the gradient formed inside the rotor, the non-retained parts which subsequently leave the rotor, through outlet 6, being put back into circulation and subsequently reintroduced into the rotor through inlet 4. It is thus possible to cause especially the particles to be purified to pass progressively inside the gradient formed within the rotor, because of the increase of their passage frequency in the gravitational field resulting from their permanent recirculation in the closed circuit. This permanent recirculation thus increases the chances of said particles of being collected into the gradient.

The circulating liquid of the solution or of the liquid vehicle of the suspension must have an overall density less than that of the gradient, even more particularly less than the minimum density defined by this gradient and the circulation flow rate must be adjusted so as not to create any turbulence inside the gradient. Because of its lower density, this liquid forms a continuous laminar flow at the surface of the core.

Figure 2:
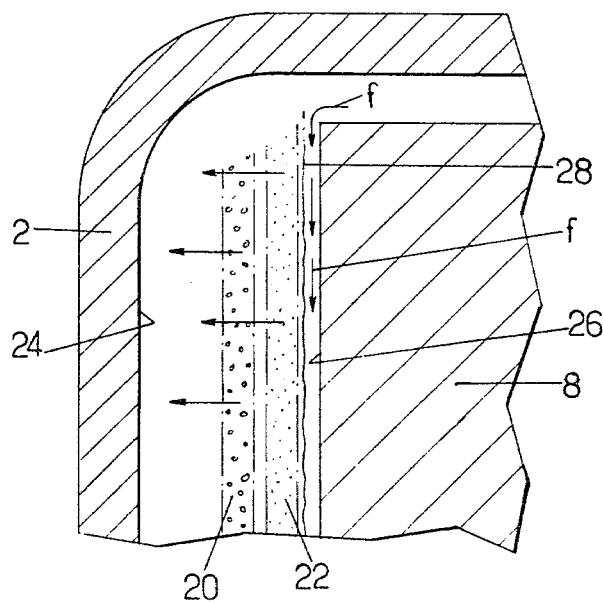
FIG. 2 is a simplified diagram the purpose of which is to explain the phenomena taking place within the centrifuge and which are to be taken into account, particularly for determining the maximum centrifugation time which must be chosen, considering the different operating parameters as a whole, particularly the nature of the particles to be purified and the gradient used.

The sole purpose of the diagram of FIG. 2 is to clarify the phenomena brought into use. This diagram may be considered as an enlarged section of the space left free in the rotor between the internal surface of this rotor 2 and the external surface of core 8, it being assumed here that the impurities have molecular or particular weights less than that of the biological particles to be purified.

The laminar flow of the circulating liquid is illustrated by the arrows f of FIG. 2. There are shown at 20 and 22 the bands in the positions which they occupy at a given moment, in which the particles to be purified on the one hand, and the impurities of the lower molecular mass, on the other hand, are gradually concentrated. It will be understood that, because of the "progressive extraction" out of the circulating liquid of the particles to be purified, said bands will move progressively towards the internal walls 24 of the rotor to the position which should correspond to the isodense band (to the extent that the gradient contains it, although this is not necessary) The band in which these particles are located tends however to gradually widen during the extraction and during its progress towards the internal surface of the rotor. The same applies to the band of possibly extracted impurities, which, because of their molecular weights will however migrate less quickly and will concentrate in a band close to the surface of the core. It is desirable to interrupt the operation from the moment when the two bands 20 and 22 tend to merge, in which case the fraction of purified particles would tend to be recontaminated by the previously separated impurities of lower molecular weight. It is then necessary, before this moment, to interrupt the circulation of the sample to be purified and the centrifugation (the circulating sample being in particular replaced by a buffer solution during the slowing-down period of the rotor) and to recover in a way known per se band 20 enriched with biological particles.

In accordance with a preferred embodiment of the process of the invention, the gradient is formed by a solution having a higher degree of viscosity than the liquid vehicle of the solution or suspension of particles to be purified, on the one hand, so as to delay migration towards the walls of the rotor of the impurities to be separated and, on the other hand, so that the laminar flow of the circulating liquid disturbs as little as possible the gradient as a whole.

To this end, it is advantageous to use for forming the gradient a solution of an organic material, particularly a polyol, such as saccharose (sucrose) or glycerol or, generally, any suitable material (having a non-precipitating character with respect to the particles to be purified), whereas the material to be purified will be contained in a solution having a lesser viscosity and a lesser density possibly diluted in an appropriate buffered saline solution. When the particles to be purified are formed by the HBs antigen, plasma or serum extracts may be used, preferably previously freed of a first part of the impurities which normally accompany it in the serum, such as immuncomplexes and lipoproteins.

The viscosity differences of the liquids under consideration, then cause a "viscosity discontinuity" shown symbolically by line 28 in FIG. 2 between the laminar flow sliding along core 8 and the density gradient retained inside the rotor.

This viscosity discontinuity then allows the laminar flow to slide along the density gradient without appreciable disturbance of the bands containing the lightest fractions, particularly the impurities (bands 22 in the diagram of FIG. 2).

Such an operation allows rapid separation of particles to be purified, even when they are characterized by low particulate weights. Moreover, a particularly favorable ratio of quantity of material purified to centrifugation time is obtained.

Additional purifications may be performed by repeating the same operation on the fraction obtained at the end of a first operation of the type which has been defined above. These operations may be repeated as long as necessary until a desired purification rate is obtained. Advantageously, when a first level of enrichment or purification has been attained, the last fraction recovered may also be subjected to isopycnic fractionation under conditions known per se. Considering the degree of purification which the process of the invention allows to be obtained, it will however be possible to effect this isopycnic fractionation in centrifuges of smaller size, resulting in a further gain from the economic point of view.

As will be illustrated hereafter, the purification of an HBs antigen concentrate may be achieved under particularly satisfactory conditions, when it is subjected to two rate zonal banding fractionation steps in accordance with the process of the invention and to a final isopycnic banding operation.

The invention applies with particular advantage to the purification of all biological particles having relatively low particulate weights particularly less than 20,000,000. It is known in fact that the conventional rate zonal banding process, in open circuit (continuous feeding of the rotor with the suspension or solution to be purified and continuous discharge of the effluents), becomes practically inapplicable for particles or organized agglomerates of particles having molecular or particulate weights less than 20,000,000.

For defining the type of molecules of the particles to be purified to which the invention advantageously applies, recourse may also be had to their sedimentation constants. In particular, the invention applies advantageously to molecules or particles characterized by sedimentation constants less than 200 Svedbergs.

By way of nonlimiting examples of the particles to which the invention applies, besides the BHs antigen (particulate weight of the order of 2,000,000; 40 Svedbergs), the following may be mentioned: the picornaviruses, the poliomyelitis virus (about 150 Svedbergs), the virus of aphtous fever (foot-and-mouth disease) (about 140 Svedbergs), virus envelopes, etc.

Although the indications which follow must not be considered as having the least limiting character, it may be mentioned that the process of the invention allows good separations in a single operation when the suspension circulated in the closed circuit and the volume of the gradient are in a ratio ranging from 0.5 to 5. Of course, a man skilled in the art will have to take into account in a way known per se, for adjusting the circulation flow rate, parameters whose impact is known (sedimentation constants of the biological particles to be purified, on the one hand, and impurities, on the other hand, contamination levels, etc). In the particular case of the HBs antigen, this volume ratio of the sample to be treated to the volume of the gradient may advantageously range from 0.5 to 1. Obviously, one may operate with a ratio lower than the lower limit of the above-mentioned ranges. It will however be appreciated that the economic advantage of the process will be reduced thereby.

The following disclosure is a description in a nonlimiting way, of a general preferred method for purifying the HBs antigen (surface antigen of the virus of hepatitis B), with a view to its use as a vaccine. It will be remembered that this antigen is found in two types of people: on the one hand, individuals affected with type B viral hepatitis, accordingly presenting pathological signs of the illness and, on the other hand, the individuals not presenting any of these clinical signs, and generally called "healthy carriers".

The raw material used in accordance with the present invention is plasma coming either from chronic hepatic carriers or "healthy carriers".

The amount of antigen is estimated by electro-immunodiffusion, by passive hemagglutination or by radio-immunoassay.

The HBs antigen in accordance with the invention is purified by one to two rate zonal banding steps in a density gradient (for example sucrose) under the above-mentioned conditions, followed by isopycnic banding, for example on a CsCl gradient. The HBs antigen subjected to these fractionation steps may come either from plasma, or from the serum obtained by defibrination of plasma, or from serum from which the lipoproteins have been partially extracted by precipitation thereof in the presence of heparin and manganese chloride for example, as is well-known to a man skilled in the art, of from serum from which the immuncomplexes and a part of the lipoproteins have been extracted after precipitation thereof by "polyethylene glycol 6000" (PEG 6000) having an average molecular weight of about 6000 (known for its efficiency insofar as separation of the immuncomplexes and lipoproteins is concerned) in an 5.5% concentration (weight/volume of antigenic preparation).

As starting raw material the supernatant of serum having been subjected to a "PEG 6000" precipitation will be preferred.

Rate zonal banding is carried out conveniently in a centrifuge of the "ELECTRO-NUCLEONICS" type "K" or "RK". The immobile rotor equipped with a continuous-flow core is filled with a saline solution, then a quantity of dense solution, for example 40% sucrose, is introduced through the bottom of the rotor driving out 50% of the initial volume of saline solution. The speed of the rotor is increased so that a sucrose gradient is established by dynamic reorientation. Typically, the extreme concentrations of the self-formed gradient are 40% and 7% sucrose.

When the desired speed of the rotor is reached, the centrifuge is connected into the above mentioned closed circuit, the medium containing the HBs antigen is introduced either through the bottom or the top of the the rotor (the direction of circulation being immaterial), by means of a pump.

The centrifugation time is defined depending on the volume of the sample treated for a given speed. A centrifugation time at 35,000 revolutions/minute will be preferably chosen for a sample volume being treated equal to half the gradient volume.

The injection flow rate of the sample into a closed circuit has little influence on the efficiency of the fractionation. A flow rate of 5 to 10 liters per hour is typically used.

When the desired centrifugation time has been reached, the rotor is stopped under conditions, known to the man skilled in the art, which allow good reorientation of the gradient. After fractionation of the contents of the rotor, the richest fractions in HBs antigen are collected. The less rich fractions, as well as the effluent are collected and may be retreated in the same way after concentration, by ultrafiltration for example.

The antigen purified and enriched by a first zonal rate banding may be subjected again to a second rate zonal banding fractionation under the same conditions as previously.

Typically, the product resulting from a first rate zonal banding has a protein content 25 times less than the initial product. When this resulting product is subjected to a second rate zonal banding the fraction of HBs antigen enriched gradient contains a quantity of proteins 12 times less than the intermediate product. Thus two successive rate zonal banding cycles generally lead to a purified and AgHBs-enriched preparation containing 300 times less proteins than the initial product.

The antigen thus purified, preferably by two successive rate zonal bandings, is subjected to isopycnic banding in a zonal centrifuge. Although identical results may be obtained with any suitable salt, cesium chloride is preferably chosen which is known to lower the infectiveness of viral particles which may possibly be present.

This operation is conveniently carried out in the rotor of the type known under the name "MSE BXIV" or "BXV" for example, under centrifugation time and speed required and sufficient for the HBs antigen to reach its position of equilibrium, i.e. in the density range 1.17 to 1.20.

The product resulting from an antigen subjected successively to two rate zonal bandings as above defined and to an isopycnic centrifugation under the previously mentioned conditions generally contains 6000 times less proteins than the initial product.

It has been shown that the antigen of the present invention has a purity and an immunizing power (Table 1) such that it may be used as a vaccine against hepatitis B after sterilizing filtration and treatment with formaldehyde.

EXAMPLE 1

The rotor of an "ELECTRO-NUCLEONICS $K_2$" centrifuge was filled with 3.4 liters of tris-NaCl buffer; then through the bottom of the rotor, 1.7 liters of a 40% sucrose solution were introduced therein, thereby causing discharge of an equal volume of buffer from the centrifuge. The rotor speed was accelerated up to 35,000 rpm and connected into a closed circuit, in which a 2 liter sample of a supernatant from a serum that had previously been treated with 5.5% "PEG 6000" was caused to circulate by means of a pump having a delivery rate of 10 liters p.hour. The system was run for a period of 2 hours.

After stopping the rotor, one liter of AgHBs-rich material was recovered, then dialysed and subjected to a rate zonal banding in an "$RK_3$" rotor. The "$RK_3$" rotor was filled with 1.6 l of tris-NaCl buffer; then through the bottom of the rotor 0.8 l of a 40% sucrose solution was introduced, thereby expelling an equal volume of buffer therefrom. The rotor was accelerated up to 35,000 rpm and connected again in a closed circuit in which the 1 liter sample was caused to again circulate. The centrifugation was continued under the same operating conditions as described for the "$K_2$" rotor.

The AgHBs-rich material from the second rate zonal banding i.e. 500 ml was dialysed, concentrated at 80 ml and subjected to isopycnic banding in a cesium chloride gradient. A "BXIV" rotor, rotating at 2500 rpm, was filled with the following gradient:
1—150 ml of CsCl solution d=1.15
2—150 ml of CsCl solution d=1.228
3—150 ml of CsCl solution d=1.298
4—200 ml of CsCl solution d=1,405

The AgHBs-rich material coming from the rate zonal banding steps was injected through the heart of the rotor; 80 ml of cesium chloride solution of density d32 1.405 were discharged back to the periphery. The rotor was accelerated to 40,000 rpm and maintained at this speed for 20 hours.

After stopping the rotor, 80 ml of purified antigen were collected in a band corresponding to a mass volume ratio range of 1.17 to 1.20 g/cm$^3$.

EXAMPLE 2

Four liters of the supernatant of a serum that had been subjected to 5.5% "PEG 6000" precipitation were divided into two volumes of 2 liters, each of which were subjected to rate zonal banding in the "$K_2$" centrifuge under the conditions described in Example 1.

The AgHBs-rich fractions from the two rate zonal bandings were collected, i.e. 2 liters of material, which were subjected to a second rate zonal banding in the "$K_2$" rotor centrifuge following the method described in Example 1.

The AgHBs-rich material collected after the second rate zonal banding, i.e. 1 liter of material was dialysed and concentrated to 150 ml.

An MSE BXV rotor, rotating at 2000 rpm, was filled with the following gradient:
1—400 ml of CsCl solution d=1.15
2—400 ml of CsCl solution d=1.228
3—400 ml of CsCl solution d=1.298
4—550 ml of CsCl solution d=1.405

150 ml of purified antigen, coming from the rate zonal bandings were injected into the heart of the rotor thereby discharging 150 ml of CsCl solution of density d=1.405 back to the periphery. The centrifugation time was 28 hours at 31,000 rpm.

After stopping the rotor, 150 ml of purified antigen was collected in the band having a mass/volume ratio range 1.17 to 1.20 g/cm$^3$.

EXAMPLE 3

8 liters of the supernatant of a serum which had been previously subjected to a 5.5% "PEG 6000" precipitation was treated in four times 2 liters in the "$K_2$" rotor as described in Example 1.

The AgHBs-rich fractions coming from the four rate zonal bandings were collected i.e. in toto 4 liters of material which were divided in 2-liter volumes, respectively subjected to second rate zonal bandings in the "K₂" rotor such as described in Example 1.

The AgHBs-rich material, collected from the two rate zonal bandings, i.e. 2 liters of material, was dialysed, concentrated to 250 ml and subjected to a CsCl gradient isopycnic banding, in an MSE, BXV zonal rotor such as described in Example 2.

EXAMPLE 4

8 liters of supernatant of a serum that had previously been subjected to a 5.5% "PEG 6000" precipitation, were treated in a first cycle of two successive rate zonal bandings as described in Example 3. In addition the effluents and HBS antigen-rich fractions discarded during the first rate zonal bandings were subjected to a retreatment cycle. 18 liters of material were concentrated to a volume of 4 liters by ultrafiltration.

This concentrate was subjected to two successive rate zonal bandings in the "K₂" rotor such as described in Example 2.

The HBs antigen-rich material collected from the first rate zonal banding cycle and from the second retreatment cycle, i.e. 3 liters, was dialysed and concentrated to 250 ml. This concentrate was subjected to a cesium chloride gradient centrifugation as described in Example 2.

EXAMPLE 5

Table 2 shows the increase in yield per unit of time when the volume of treated material was increased.

EXAMPLE 6

8 liters of plasma were treated according to the procedure described in Example 4.

EXAMPLE 7

8 liters of serum were treated according to the procedure described in Example 4.

EXAMPLE 8

8 liters of supernatant of a serum mixture which had previously undergone a treatment causing precipitation of the lipoproteins by means of heparine and manganese chloride were treated according to the procedure described in Example 4.

EXAMPLE 9

8 liters of plasma mixture were subjected after defibrination and sterilizing filtration to fractionated precipitation with "PEG 6000". After a first precipitation with "PEG 6000" at a concentration of 5%, the supernatant was subjected to a second precipitation with "PEG 6000" at a concentration such that AgHBs was precipitated. For this purpose a concentration of 16% "PEG 6000" was preferably chosen. The HBs antigen-enriched sedimented residue was taken up in a tris-NaCl buffer, in a final volume of 2 liters; this sample was subjected to the successive rate zonal bandings and isopycnic bandings as described in Example 1.

TABLE 1

| Amount of proteins per injection in μg | Immunizing power on guinea pigs | |
|---|---|---|
| | % guinea pigs Positive antibody rate | Antibody rate expressed in RIA units per guinea pig |
| 12.6 | 100% | 300 |
| 6.08 | 100% | 198 |

TABLE 1-continued

| Amount of proteins per injection in μg | Immunizing power on guinea pigs | |
|---|---|---|
| | % guinea pigs Positive antibody rate | Antibody rate expressed in RIA units per guinea pig |
| 3.04 | 100% | 236 |

Method of immunization: groups of 8 guinea pigs received subcutaneously two injections of antigenic preparation at a 15 day interval; they were bled 15 days after the second injection. The anti HBs antibody rate was determined by radioimmunoassay (RIA).

TABLE 2

| Amount of plasma treated in liters | Duration of the first rate zonal banding in hours | Duration of the second rate zonal banding in hours | Duration of the isopycnic banding in hours | Total duration of rate zonal and isopycnic bandings in hours | Number of hours of centrifugation per liter of plasma treated |
|---|---|---|---|---|---|
| 2 | 2 | 2 | 20 | 24 | 12 |
| 4 | 4 | 2 | 28 | 34 | 8.5 |
| 8 | 8 | 4 | 28 | 40 | 5 |

In the preceding disclosure:

the densities or mass/volume ratios of particles are expressed with respect to cesium chloride solutions;

the percentages of any constituent are expressed in weight per volume of the whole preparation in which they are contained.

We claim:

1. In a process for purifying or concentrating biological particles in a liquid composition containing said biological particles in a solution or suspension wherein said liquid composition is subjected to rate zonal banding by centrifugation in a gradient within a centrifuge, the improvement which comprises purifying said liquid composition by continuously circulating said liquid composition in a closed circuit into and out from the centrifuge, wherein said centrifuge is part of said closed circuit, the continuous circulation is carried out at the same time as the centrifugation is carried out and the rate and period of circulation are such that said liquid composition is recirculated through said centrifuge and part of the particles in said liquid composition is collected by the gradient at each passage.

2. The process of claim 1, wherein said gradient is formed by a solution having a higher degree of viscosity than the solution or suspension of particles to be purified.

3. The process of claim 1 wherein said gradient is formed by a solution of sucrose having a sucrose content which varies in the gradient from 7% to 40%.

4. The process of claim 1 wherein the volume of said liquid composition continuously treated in the same operation and the gradient volume are in ratio of from 0.5 to 5.

5. The process of claim 1 wherein the volume of said liquid composition continuously treated in the same operation and the gradient volume are in ratio of from 0.5 to 5 and wherein the gradient occupies at least 9/10 of the centrifuge internal capacity.

6. The process of claim 1 wherein the volume of said liquid composition continuously treated in the same operation and the gradient volume are in ratio of from 0.5 to 1.

7. The process of claim 1 wherein the volume of said liquid composition continuously treated in the same operation and the gradient volume are in ratio of 0.5 to 1 and wherein the gradient occupies at least the 9/10 of the centrifuge internal capacity.

8. The process of claim 1, 2, 3, 4, 5, 6 or 7 wherein the biological particles to be purified have particulate weights less than 20,000,000 or sedimentation constants less than 200 Svedbergs.

9. The process of claim 1, 2, 3, 4, 5, 6 or 7, wherein the biological particles to be purified or concentrated are formed of the HBs antigen.

10. The process of claim 9 which comprises subjecting the purified or concentrated fraction resulting from said rate zonal banding to at least a second rate zonal banding by continuously circulating said fraction of a closed circuit including said centrifuge, wherein the continuous circulation is carried out at the same time as the centrifugation is carried out and the rate and period of circulation are such that said liquid composition is recirculated through said centrifuge and part of the particles in said liquid composition is collected by the gradient at each passage, and collecting the further enriched HBs antigen.

11. The process of claim 9 which comprises subjecting the purified or concentrated fraction resulting from said rate zonal banding to at least a second rate zonal banding by continuously circulating said fraction in a closed circuit including said centrifuge, wherein the continuous circulation is carried out at the same time as the centrifugation is carried out and the rate and period of circulation are such that said liquid composition is recirculated through said centrifuge and part of the particles in said liquid composition is collected by the gradient at each passage, collecting the further enriched HBs antigen,
subjecting a solution or suspension of further enriched HBs antigen to isopycnic banding in a cesium chloride density gradient and
collecting a purified HBs antigen-fraction from the band of said cesium gradient of mass/volume ratios ranging from about 1.17 $g/cm^3$ to about 1.20 $g/cm^3$.

12. The process of claim 9, wherein the solution or suspension containing the HBS antigen is formed of a human plasma, a serum obtained by defibrination of human plasma or a medium containing the elements of said plasma or serum freed of the major part of the immuncomplexes and at least a part of the lipoproteins which accompanied the HBs antigen in the initial plasma or serum.

13. The process of claim 9, wherein said solution or suspension is formed of the supernatant resulting from the treatment of a serum after a precipitation treatment with a polyethylene glycol having an average molecular weight of about 6 000 in a proportion of 5.5% (weight of polyethylene glycol/volume of mixture).

14. The process of claim 9 wherein said solution or suspension is formed of a suspension in a buffered saline of the sediment obtained by a method comprising treating a serum with a 5.5% polyethylene glycol having an average molecular weight of about 6,000, in a proportion of about 5.5% (weight/volume), recovering the supernatant, subjecting the latter to a precipitation treatment with said polyethylene glycol in a proportion of 16% (weight/volume) to produce said sediment.

15. The process of claim 1 wherein said gradient in said centrifuge is formed by liquid gradient having a viscosity sufficiently different from the viscosity of said liquid composition of biological particles that laminar flow of said liquid composition of biological particles slides along said liquid gradient in said centrifuge substantially without disturbing said gradient.

16. The process of claim 1 wherein said liquid composition is recirculated several times through said centrifuge.

* * * * *